(12) United States Patent
Kim (10) Patent No.: US 9,474,545 B1
(45) Date of Patent: Oct. 25, 2016

(54) APPARATUS AND METHOD FOR SELECTIVELY ARRESTABLE MANUARY ACCESS TO SUFFLATED BODY CAVITY

(71) Applicant: H. Charles Kim, Towson, MD (US)

(72) Inventor: H. Charles Kim, Towson, MD (US)

(*) Notice: Subject to any disclaimer, the term of this patent is extended or adjusted under 35 U.S.C. 154(b) by 309 days.

(21) Appl. No.: 14/210,820

(22) Filed: Mar. 14, 2014

Related U.S. Application Data (60) Provisional application No. 61/787,460, filed on Mar. 15, 2013.

(51) Int. Cl.
*A61B 17/34* (2006.01)
*A61B 17/02* (2006.01)

(52) U.S. Cl.
CPC ........... *A61B 17/3423* (2013.01); *A61B 17/02* (2013.01)

(58) Field of Classification Search
CPC .... A61B 1/32; A61B 17/02; A61B 17/0206; A61B 17/0218; A61B 17/0231; A61B 17/025; A61B 17/0281; A61B 17/34; A61B 17/3423; A61B 2017/0212; A61B 2017/0225; A61B 2017/0237; A61B 2017/0243; A61B 2017/0256; A61B 2017/0262; A61B 2017/0268; A61B 2017/0275; A61B 2017/0287; A61B 2017/3425; A61B 2017/3427; A61B 2017/3429
USPC ................................................. 600/201–210
See application file for complete search history.

(56) References Cited

U.S. PATENT DOCUMENTS

| 4,069,913 A * | 1/1978 | Harrigan ................ A61B 42/50 |
| | | 128/856 |
| 4,964,174 A * | 10/1990 | Martin ................ A41D 19/015 |
| | | 2/161.8 |

(Continued)

*Primary Examiner* — Christian Sevilla
*Assistant Examiner* — Eric S Gibson
(74) *Attorney, Agent, or Firm* — Rosenberg, Klein & Lee (57) ABSTRACT

There is provided an apparatus (10) and method for establishing and maintaining in selectively arrestable manner manuary access to a sufflated body cavity of a patient through a fenestration formed in the patient's body tissue during a minimally invasive surgical procedure. The apparatus (10) generally comprises a seal section (100) and a sheath section (200) coupled thereto. The seal section (100) includes an endless loop portion (110) that defines an opening (120). The sheath section (200) includes a mouth portion (210), an outer glove portion (230), and a pliable intermediate portion (220) extending therebetween. The outer glove portion (230) defines a plurality of extensions to accommodate the digits of a user's hands which are truncated so that they each terminate at a digit opening. When a surgically gloved hand (2) of the user is then inserted into the outer glove portion (230), all or most of the thumb and fingers of the gloved hand pass through the corresponding digit opening (232a-232e, 232a') so that the surgically gloved thumb and fingers (2) are exposed beyond the outer glove portion (230). The intermediate portion (220) maintains in reconfigurable manner a substantially gas impermeable barrier between the mouth and outer glove portions (210, 230) when the outer glove portion (230) is passed through the opening (120) into the body cavity responsive to manuary actuation. The passage of the outer glove portion (230) through the opening (120) biases at least a part of the intermediate portion (220) to engage the patient's body tissue immediately bounding the fenestration, whereby the sufflation of the body cavity is substantially preserved during the minimally invasive surgical procedure.

19 Claims, 9 Drawing Sheets

(56) References Cited

U.S. PATENT DOCUMENTS

| | | | | |
|---|---|---|---|---|
| 5,402,536 A * | 4/1995 | Matthews | A41D 13/08 2/16 |
| 5,480,410 A * | 1/1996 | Cuschieri | A61B 17/0218 606/201 |
| 5,522,791 A * | 6/1996 | Leyva | A61B 17/0293 600/207 |
| 5,582,620 A * | 12/1996 | Hirsch | 2/161.7 |
| 5,636,645 A * | 6/1997 | Ou | A61B 17/3423 128/898 |
| 5,741,298 A * | 4/1998 | MacLeod | A61B 17/00234 604/174 |
| 5,813,409 A * | 9/1998 | Leahy | A61F 5/445 128/850 |
| 5,853,395 A * | 12/1998 | Crook | A61B 17/3423 600/208 |
| 5,906,577 A * | 5/1999 | Beane | A61B 17/0293 600/206 |
| 6,033,426 A * | 3/2000 | Kaji | A61B 17/3423 600/207 |
| 6,033,428 A * | 3/2000 | Sardella | A61B 17/3423 606/213 |
| 6,440,063 B1 * | 8/2002 | Beane | A61B 17/0293 600/206 |
| 6,471,714 B1 * | 10/2002 | Kim | A61B 17/3423 128/850 |
| 6,485,467 B1 * | 11/2002 | Crook | A61B 17/3423 604/174 |
| 6,539,549 B1 * | 4/2003 | Peters, Jr. | A41D 19/0075 15/227 |
| 6,578,577 B2 * | 6/2003 | Bonadio | A61B 17/3423 128/850 |
| 6,582,364 B2 * | 6/2003 | Butler | A61B 1/32 600/208 |
| 6,589,167 B1 * | 7/2003 | Shimomura | A61B 17/3423 128/897 |
| 6,908,430 B2 * | 6/2005 | Caldwell | A61B 17/3423 600/207 |
| 7,008,377 B2 * | 3/2006 | Beane | A61B 17/0293 600/206 |
| 7,195,590 B2 * | 3/2007 | Butler | A61B 17/0293 600/206 |
| 7,214,185 B1 * | 5/2007 | Rosney | A61B 17/3423 600/208 |
| 7,246,382 B2 * | 7/2007 | Plut | A41D 19/0055 2/161.6 |
| 7,473,221 B2 * | 1/2009 | Ewers | A61B 17/0293 600/208 |
| 7,766,824 B2 * | 8/2010 | Jensen | A61B 17/3423 600/208 |
| 7,819,800 B2 * | 10/2010 | Beckman | A61B 17/3423 600/201 |
| 7,837,612 B2 * | 11/2010 | Gill | A61B 1/32 600/201 |
| 8,112,820 B2 * | 2/2012 | Johnson | A41D 19/0089 2/160 |
| 8,357,085 B2 * | 1/2013 | Shelton, IV | A61B 17/3423 600/203 |
| 8,752,553 B2 * | 6/2014 | Bonadio | A61B 17/3423 128/849 |
| 9,271,753 B2 * | 3/2016 | Butler | A61B 17/3423 |
| 9,295,459 B2 * | 3/2016 | Pingleton | A61B 17/0293 |
| 2004/0015185 A1 * | 1/2004 | Ewers | A61B 17/0293 606/213 |
| 2004/0127772 A1 * | 7/2004 | Ewers | A61B 1/06 600/212 |
| 2004/0215063 A1 * | 10/2004 | Bonadio | A61B 17/3423 600/201 |
| 2006/0030755 A1 * | 2/2006 | Ewers | A61B 17/0293 600/206 |
| 2008/0011307 A1 * | 1/2008 | Beckman | A61B 17/02 128/850 |
| 2009/0118587 A1 * | 5/2009 | Voegele | A61B 17/3423 600/206 |
| 2014/0163326 A1 * | 6/2014 | Forsell | A61B 17/3423 600/207 |
| 2014/0228951 A1 * | 8/2014 | Zochowski | A61F 2/12 623/8 |
| 2016/0008081 A1 * | 1/2016 | Forsell | A61B 17/3423 600/204 |

* cited by examiner

APPARATUS AND METHOD FOR SELECTIVELY ARRESTABLE MANUARY ACCESS TO SUFFLATED BODY CAVITY

RELATED APPLICATION DATA

This application is based on Provisional Patent Application No. 61/787,460, filed 15 Mar. 2013.

BACKGROUND OF THE INVENTION

1. Field of the Invention

The present invention is generally directed to an apparatus and method for facilitating a minimally invasive surgical procedure. More specifically, the subject apparatus and method is directed to facilitating manuary access to a sufflated body cavity during a hand-assisted laparascopic or other surgical procedure.

Minimally invasive surgical procedures such as laparascopic surgery have gained wide acceptance in various medical fields over traditional, fully invasive procedures for somewhat readily apparent reasons. Not only does the minimal invasiveness of such procedures significantly reduce the pain and stress to which a patient is otherwise subjected, they measurably reduce both the severity and duration of the recuperative period following surgery. The resulting benefits both in terms of cosmetic results and cost savings—are often quite considerable. Moreover, because they permit the required surgical manipulations to be carried out with the naturally enclosed biophysical environment at the surgery site kept substantially intact, such procedures minimize considerably the patient's exposure to potentially infectious or toxic organisms and contaminants. This, in turn, substantially minimizes the patient's risk of suffering medical complications.

In a typical laparoscopic surgical procedure, access to the surgery site—the abdominal or other internal body cavity, for instance—is gained through one or more fenestrations formed by puncturing the skin and the underlying muscle and soft tissue layers. A suitable miniature scope is introduced into the body cavity along with one or more laparoscopic instruments through shared or separate fenestrations. The surgeon may then perform the required surgical procedure by manipulating the laparoscopic instrument(s) and/or scope while acquiring visual feedback by viewing a video image of the site, as captured by the scope and reproduced on a display monitor.

As widely accepted and prevalent as they have become, however, such surgical procedures are not without their limitations. The surgeon's ability to adequately effect the precise cutting, suturing, and other very delicate surgical manipulations invariably required during laparoscopic procedures, for example, is highly dependent upon a set of critical factors including: the extensive experience and acute dexterity of the surgeon in performing the coordinated manipulations of the numerous laparoscopic instruments at hand; the degree of visibility attainable with the scope; and, the practical range of utility of the given instruments. A deficiency in any one of these factors severely obstructs the given procedure's successful completion and may, under certain circumstances, give rise to life threatening conditions. Hence, it not too infrequently becomes necessary to unexpectedly convert during the course of surgery to a fully invasive, open surgery.

Also, adhesions between the patient's internal organs at or around the surgery site tend to block or otherwise hinder the free manipulability of the laparoscopic instruments. It is difficult in such cases to maneuver an instrument between the adhering organs without potentially causing harm to either the organs or the instrument. Even where it is possible to adequately circumvent the adhering organs, much time and effort are unduly expended.

Of the more general limitations is the unavailability to the surgeon of any direct tactile sense of the surgery site. The instantaneous assessments that the surgeon must continually make as the surgical procedure progresses is consequently hindered by the lack of a key component of sensual feedback. The practicability of laparoscopic and like procedures is thus unduly restricted.

An approach developed to address these limitations is the so-called hand-assisted procedure, wherein the surgeon actually inserts a free hand into the given body cavity through a fenestration. With this free hand, the surgeon is able to supplement indirect, instrument-effected manipulations of organ and tissue parts with direct, hand-effected manipulations. Such direct hand manipulations often aid enormously in effecting difficult manipulations of organ and tissue that may otherwise be problematic using laparoscopic instrument maneuvers alone. With the free hand, the surgeon is also able to supplement the visual feedback acquired via the laparascopic scope with tactile sense feedback. Such supplemental feedback yields a vital source of additional information for either confirming or correcting visual assessments which, alone, may leave lingering ambiguity and general uncertainty.

While this manuary access to the surgery site greatly facilitates the conduct of minimally invasive surgical procedures, it too presents significant potential drawbacks and difficulties. First and most obvious, it necessarily compromises to some unavoidable extent the minimal invasiveness of the procedures. More notable than that, however, the sizable fenestration necessary to accommodate the manuary access threatens to compromise the body cavity's vital sufflation.

Consequently, there is a need for a method and apparatus by which a surgeon may safely and securely gain manuary access to an internal body cavity during a hand-assisted minimally invasive surgical procedure. There is a need for such method and apparatus that sufficiently establishes and maintains a substantially airtight seal across the fenestration which admits the surgeon's hand into the body cavity, yet does not unduly restrict or restrain the hand's movements. There is, furthermore, a need for such method and apparatus which is simple, convenient, and economical to utilize.

There is a further need for such method and apparatus by which the manuary access may be temporarily arrested, so that a surgeon may safely and conveniently remove his/her hand from the internal body cavity without substantial loss of seal across the fenestration or compromise of sterility. There is a need for this type of method and apparatus that permits the same surgeon or another surgeon/colleague to then re-insert their hand into the internal body cavity, re-establish manuary access without loss of seal or sterility, and resume the procedure.

2. Prior Art

Devices are known in the art for facilitating manuary access to an internal body cavity during hand-assisted laparoscopic surgical procedures. The inventor's own prior U.S. Pat. No. 6,471,714 is directed to such manuary access to sufflated body cavity. The disclosed approach provides highly effective manuary access when the disclosed apparatus is used continually during a procedure.

For instance, in U.S. Pat. No. 5,853,395 issued to Crook et al., an assembly is disclosed for providing extracorporeal pneumoperitoneum. The assembly includes a multi-part support ring structure which is adhesively affixed to the patient's abdominal surface surrounding the given fenestration; a collar-like wound protector which is inserted to line the exposed edges of the fenestration; and a flexible sleeve member about an open end of which a seal ring is attached. During use, the seal ring of the sleeve member is secured in sealed manner to the ring structure. The surgeon's hand, wearing a surgical glove, is passed to engage finger holes formed into an otherwise closed end of the sleeve member, then advanced first through the engaged seal ring and its supporting ring structure, and next through the wound protector, into the internal body cavity. The gas escaping through the fenestration is captured by the sleeve member, which is sealed and retained in place cooperatively by the seal ring and supporting ring structure.

While this assembly does enable manuary access to the internal body cavity, and even seeks to preserve pneumoperitoneum during that access, it nonetheless suffers from a number of very notable drawbacks which, in practice, diminish its utility. First, the assembly is quite substantial both in the number and complexity of its components. This not only further complicates matters for the surgeon already burdened by the numerous concerns relating to the surgical procedure at hand, it makes for a cumbersome structure that consumes an inordinate share of the precious area on the surface of the patient's abdomen—area necessary to adequately accommodate fenestrations for the passage of other instruments into the internal body cavity. Second, proper operation of the assembly hinges upon the support ring structure remaining adhesively affixed to the patient's abdominal skin surface throughout the surgical procedure which typically lasts hours on end. During the course of surgery, however, the cumulative effects of moisture, movements of the surgeon's hand, and other factors often erode the structure's adhesiveness to the point that it actually detaches from the patient's skin surface, thereby compromising the seal and openly exposing the surgery site to contaminants. What is more, adequate remedial measures are not readily available at that point, for it is extremely difficult to re-adhere the structure to the skin surface once adhesion is initially lost.

An additional drawback of note is the presence of openings in the form of finger holes formed at one end of the sleeve member. The material composition and makeup of the sleeve member is such that the holes not only require the surgeon's hand be covered by an inner surgical glove prior to passage of the fingers and thumb therethrough, and an outer surgical glove following passage of the fingers and thumb therethrough. The tightly fitting extraneous layers thus required about the surgeon's hand, in addition to being highly inconvenient to adorn, very undesirably constrict the surgeon's hand and constrain its movements—consequently heightening the discomfort experienced by the surgeon as well as the effort exerted by him or her. The extraneous layers also dull the covered hand's sensitivity, severely limiting the degree of useful sensual feedback that the surgeon might otherwise acquire by touch.

Another device known in the art is one disclosed in U.S. Pat. No. 5,480,410 issued to Cuschieri et al. for an extracorporeal pneumoperitoneum access bubble. The device forms a balloon-like spherical dome structure having a bottom opening whose neck is passed through a fenestration to serve as a conduit for insufflation gas migrating from the abdominal cavity. Thus maintained in an inflated state, the dome portion has formed therein a plurality of valves which permit access to various instruments without permitting significant leakage of the insufflation gas.

The device permits access also to a surgeon's hand, provided that the admitting valve formed in the dome portion is of sufficiently great size. The device, nonetheless, suffers from a number of the practical drawback s suffered by other similar devices known in the art. First and most obvious, the valve openings which permit access to instruments as well as the surgeon's hand necessarily interrupt the gas impermeable barrier extending over and about the fenestration. While they are designed to minimize it, the valve openings invariably permit leakage when accommodating an implement passed therethrough, especially since they are subjected to disturbing forces by the implements' manipulation during a given surgical procedure. This leakage would occur all the more where a valve opening is of extraordinary size—as it must be to accommodate the surgeon's hand and forearm; and where a valve opening is subjected to a substantial degree of disturbance—as would be caused by the surgeon's hand and forearm movements.

Another drawback is found in the considerable space necessarily occupied by the device's dome portion. The expansive volume permits few, if any, other instruments to share surrounding areas of the patient's abdominal skin surface. Indeed, the plurality of valve openings formed in the dome portion seemingly encourages common use of the device to admit multiple instruments into the abdominal cavity. Where additional instruments must be introduced into the abdominal cavity through neighboring fenestrations, in any event, the task becomes rather awkward, with the prevailing likelihood—even if neighboring instruments may be adequately introduced—of inadvertently making interfering contact with them.

Yet another drawback resides in the lack of adequate measures for maintaining the device sufficiently in place. As the insufflation gas migrates into and collects within its dome portion, the device is internally subjected to the intra-abdominal pressure that maintains insufflation of the abdominal cavity. With its resulting balloon-like structure, then, the device becomes somewhat unstable in its disposition, and tends in practice towards expulsion from its engagement with the fenestration.

SUMMARY OF THE INVENTION

It is a primary object of the present invention to provide an apparatus and method whereby a surgeon may safely and securely gain manuary access to an internal body cavity during a hand-assisted minimally invasive surgical procedure.

It is another object of the present invention to provide an apparatus and method whereby a substantially air-tight seal is substantially maintained across a fenestration that admits a surgeon's hand into an internal body cavity during a hand-assisted minimally invasive surgical procedure.

It is yet another object of the present invention to provide an apparatus and method whereby manuary access to an internal body cavity may be gained without undue restriction or restraint of the surgeon's hand movements.

It is still another object of the present invention to provide an apparatus and method which is both simple and convenient to utilize.

It is another object of the present invention to provide an apparatus and method by which the manuary access to an internal body cavity may be established then temporarily arrested for safe removal and replacement of the accessing hand.

These and other objects are attained in the apparatus and method of the present invention for maintaining manuary access to a sufflated body cavity through a fenestration formed through a patient's body tissue during a minimally invasive surgical procedure. The apparatus generally comprises a seal section and a sheath section formed of a substantially gas impermeable material coupled thereto. The seal section includes an endless loop portion defining a first opening. The loop portion is formed with an engagement surface for engaging in substantially flush manner an inner wall surface of the sufflated body cavity adjacent the fenestration. The sheath section includes a mouth portion, an outer glove portion, and a pliable intermediate portion collapsibly extending therebetween. The outer glove portion defines a plurality of extensions to accommodate the digits of a user's hands which are truncated so that they each terminate at a digit opening. Preferably, a first extension admits the user's thumb, while a second extension receives admits the user's remaining digits together. Among the advantages offered by such truncated mitten type configuration is provision for a somewhat universal, one size fits all, offering to users having a wide range of hand sizes and finger thicknesses/lengths. In certain other configurations, a plurality of additional extensions may be provided in addition to the first, thumb, extension to accommodate individual fingers. Such configurations may preserve numerous advantages, but may not be as universally adaptable to users with different sized hands and finger thicknesses.

When a surgically gloved hand of the user is then inserted into the outer glove portion, much of the thumb and fingers of the gloved hand pass through the corresponding extension openings so that the surgically gloved thumb and fingers are exposed beyond the outer glove portion, free and clear of any additional layering that the outer glove portion might otherwise cover them with. During use, the surgically gloved hand (the surgical glove effectively forming an inner glove for the user) is snuggly fitted within the outer glove portion to make sealed engagement with the surrounding parts of that outer glove portion.

The mouth portion is coupled to the loop portion of the seal section and defines a second opening aligned in open communication with the first opening. The intermediate portion maintains in reconfigurable manner a substantially gas impermeable barrier between the mouth and glove portions when the outer glove portion is passed through the first and second openings into the body cavity responsive to manuary actuation. This passage of the outer glove portion through the mouth and loop portions sufficiently deflects sufflation gas to bias at least a part of the intermediate portion into substantially conforming engagement of the patient's body tissue peripherally bounding the fenestration. The sufflation of the body cavity is thus substantially preserved during the minimally invasive procedure.

During use, when the user wishes to temporarily interrupt the manuary access for any reason (to rest, to make way for another surgeon to make manuary access and continue the procedure, . . . ), he/she may withdraw the accessing hand from the internal body cavity. The outer glove portion will then pull back out with the hand through the mouth portion which remains in sealed engagement within the body cavity. Part of the intermediate portion also pulls back out with the outer glove portion essentially for inside out withdrawl through the mouth portion. The surgeon may then grasp the withdrawn part of the intermediate portion to pinch and constrict the same there. This substantially holds the sufflation seal in tact and permits the surgeon to de-couple and fully remove the surgically gloved hand (just withdrawn from manuary access) from the outer glove portion. The surgeon or another individual may then replace a surgically gloved hand back into the outer glove portion, appropriately adjust the fit, then re-insert that outer glove portion and the trailing intermediate portion back with the gloved hand in through the mouth portion and into the internal body cavity to resume manuary access for the given procedure.

Generally, an apparatus is provided for maintaining manuary access to a sufflated body cavity through a fenestration in selectively arrestable manner during a minimally invasive surgical procedure. The apparatus comprises a seal section including an endless loop portion defining a first opening, wherein the loop portion has formed thereon an engagement surface for engaging in substantially flush manner an inner wall surface of the sufflated body cavity adjacent the fenestration. A sheath section is formed of a substantially gas impermeable material. The sheath section includes a mouth portion coupled to the loop portion of the seal section, wherein the mouth portion defines a second opening aligned in open communication with the first opening. An outer glove portion defines at least two digit receiving sections each terminated by a truncation opening for respectively passing the thumb and fingers of a user's gloved hand and resiliently engaging in sealed manner the base portions thereof. A pliable intermediate portion extends between the mouth and outer glove portions to maintain therebetween a substantially gas impermeable barrier for defining a gas capturing pocket when the outer glove portion is passed through the first and second openings into the body cavity responsive to manuary actuation. The gas capturing pocket receives sufflation gas migrating from the body cavity to distend adaptively about the outer glove portion; whereby the sufflation of the body cavity is substantially preserved during the minimally invasive procedure.

DETAILED DESCRIPTION OF THE PREFERRED EMBODIMENTS

In broad overview, the apparatus and method of the present invention improves upon known approaches to establishing manuary access to a patient's internal body cavity. The subject apparatus is configured for use by a surgeon or other health care professional having his/her accessing hand already wearing a surgical glove. The subject apparatus provides an outer glove portion formed with much the same structure as in the glove of the inventor's own prior U.S. Pat. No. 6,471,714. But the fingers and thumb portions of the outer glove portion are truncated, with their tips effectively cut away. Truncating these digit sections of the outer glove portion at or near their base enables a surgeon or other health practitioner to put a surgical glove over their hand, and insert the gloved hand into the outer glove portion preferably with his/her gloved thumb passing through one truncated digit opening and gloved fingers passing collectively through another shared truncated digit opening. In certain other embodiments, the gloved fingers may pass through respective truncated digit openings. The material composition and properties of the outer glove portion are such that the truncated digit openings resiliently engage in sealed manner the base portions of the thumb and finger(s) passing therethrough.

FIGS. 1, 1A, 1B, 2, and 2A of the drawings illustrate some of the advantages this provides. There are a number of the reasons for using this multi-gloved approach. First, surgeons use this outer glove device, while wearing another surgical glove on their hand (worn before they put it inside this glove device). The manuary access to sufflated body cavity provided by the outer glove structure (much as in the '714 glove) is highly advantageous. But the multiple glove layers could cause hindrance at the extremities of his/her fingers—at and above the fingertips. It is obviously very important for a surgeon to maintain maximum flexibility and sensitivity of the thumb, fingers, and their tips, in order that the surgeon may carry out the required surgical hand manipulations inside the body cavity (for instance the abdominal cavity of the patient). Both flexibility and sensitivity are hindered with each additional glove layer.

The outer layer of glove covering is therefore removed from the surgeon's fingers and thumbs. Thus, when the surgeon puts his/her already gloved hand in through this new and improved device, the portions around the wrist and the base of the hand are covered and in tight elastic, preferably sealed engagement with the outer glove portions there. So the seal provided by the outer glove portions are not lost there. At the same time, the fingers and the thumbs emerge out of the outer glove free and clear of the outer glove material, such that the surgeon's thumb and fingers remain largely free of the additional glove layer material. Flexibility and sensitivity of the surgeon's thumb and fingers are unabated by the outer glove, and the surgeon may carry out a procedure with the same dexterity and sensitivity as if he/she were doing so without any intervening outer glove apparatus.

Sterility: Preserving a Sterile Environment

Usually when a surgical team operates on a patient, the lead surgeon may start the procedure and his/her hand may be inserted into a sufflated body cavity of the patient. At some point though, the need may arise for this surgeon to remove his/her hand from manuary access. The surgeon may need to rest or otherwise break temporarily from the procedure. Alternatively, another surgeon or other colleague may need to resume the manuary access by inserting their hands in place of the first surgeon's. In this case, since the first surgeon had worn an inner glove (rather than inserting his/her bare hand in a prior outer glove/manuary access device of the type disclosed by the '714 patent), sterility is preserved even if he/she pulls the hand out. Sterility would be lost otherwise, had the surgeon removed an unprotected bare hand because the bare hand would have contaminated the inside of such prior outer glove/manuary access device. Such would have precluded any shared manuary access between surgeons through the same portal provided by the device. With the device disclosed herein, sterility of the outer glove portion is preserved, where another's gloved hand is placed back into the outer glove portion once the first surgeon's gloved hand is removed therefrom.

Figure 2:
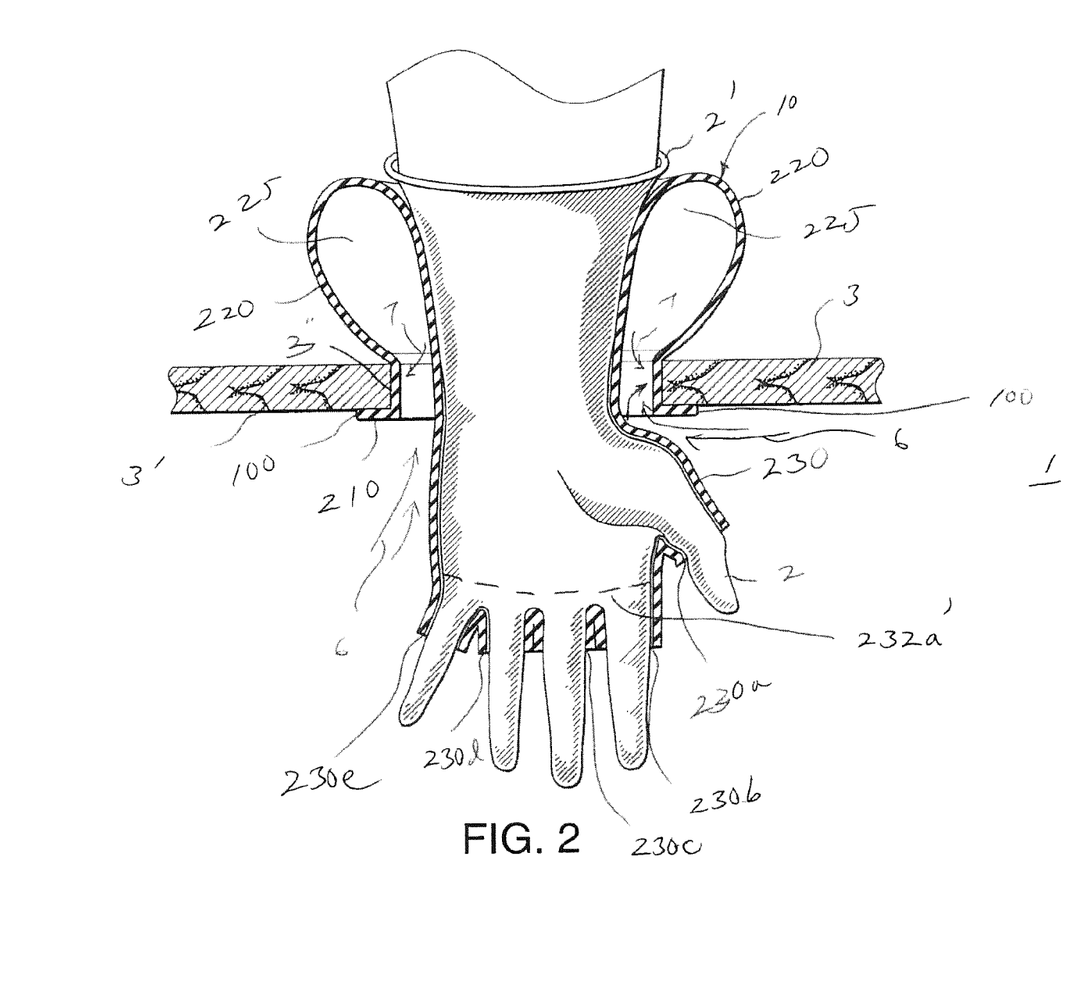
FIG. 2 is a sectional view comparatively showing the embodiments of FIGS. 1 and 1A, illustrated in an exemplary configuration during manuary access.
Figure 2A:
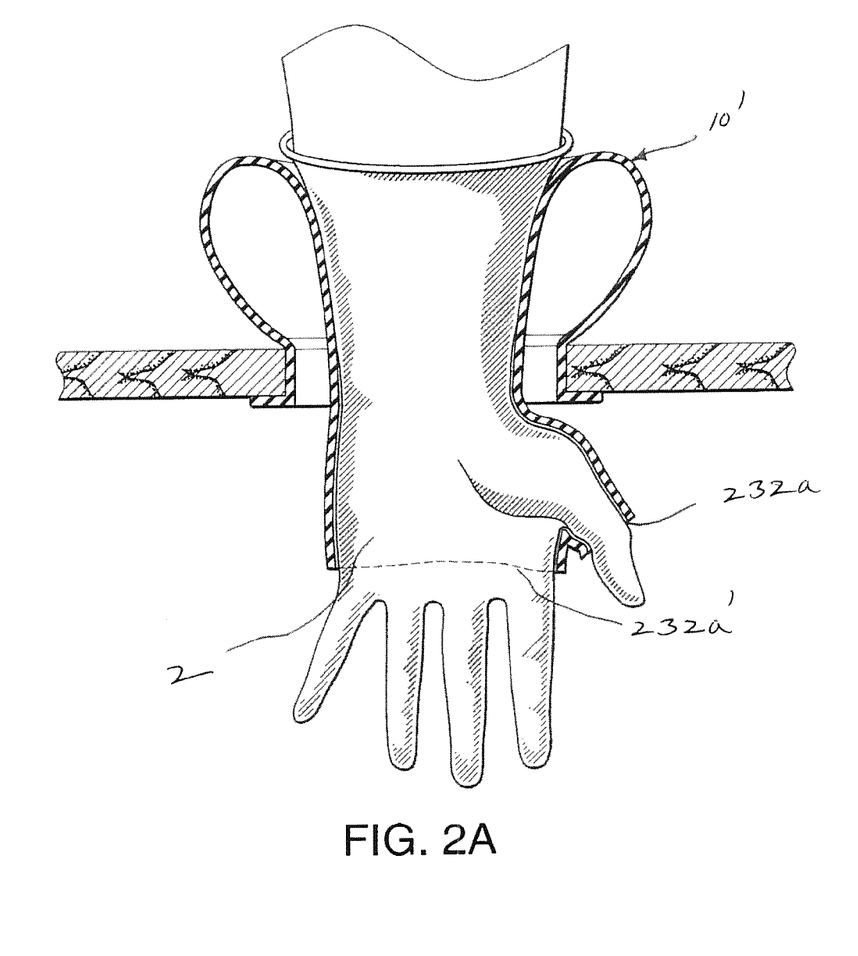
FIG. 2A is a sectional view showing the embodiment of FIG. 1A, illustrated in an exemplary configuration during manuary access.
Figure 6:
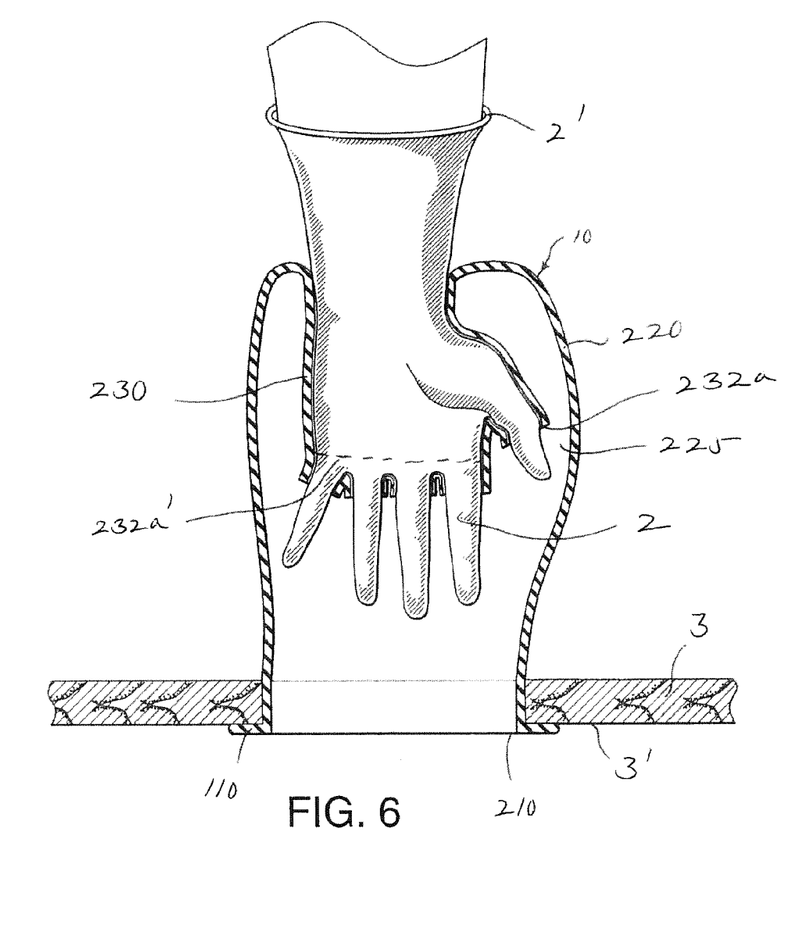
FIG. 6 is a sectional view comparatively showing the embodiments of FIGS. 1 and 1A, illustrated in an exemplary configuration during withdrawal of the user's gloved hand from manuary access; and, FIG. 7 is a sectional view comparatively showing the embodiments of FIGS. 1 and 1A, illustrated in an exemplary configuration after removal of the user's gloved hand therefrom, following withdrawal from manuary access as illustrated in FIG. 6.
Figure 7:
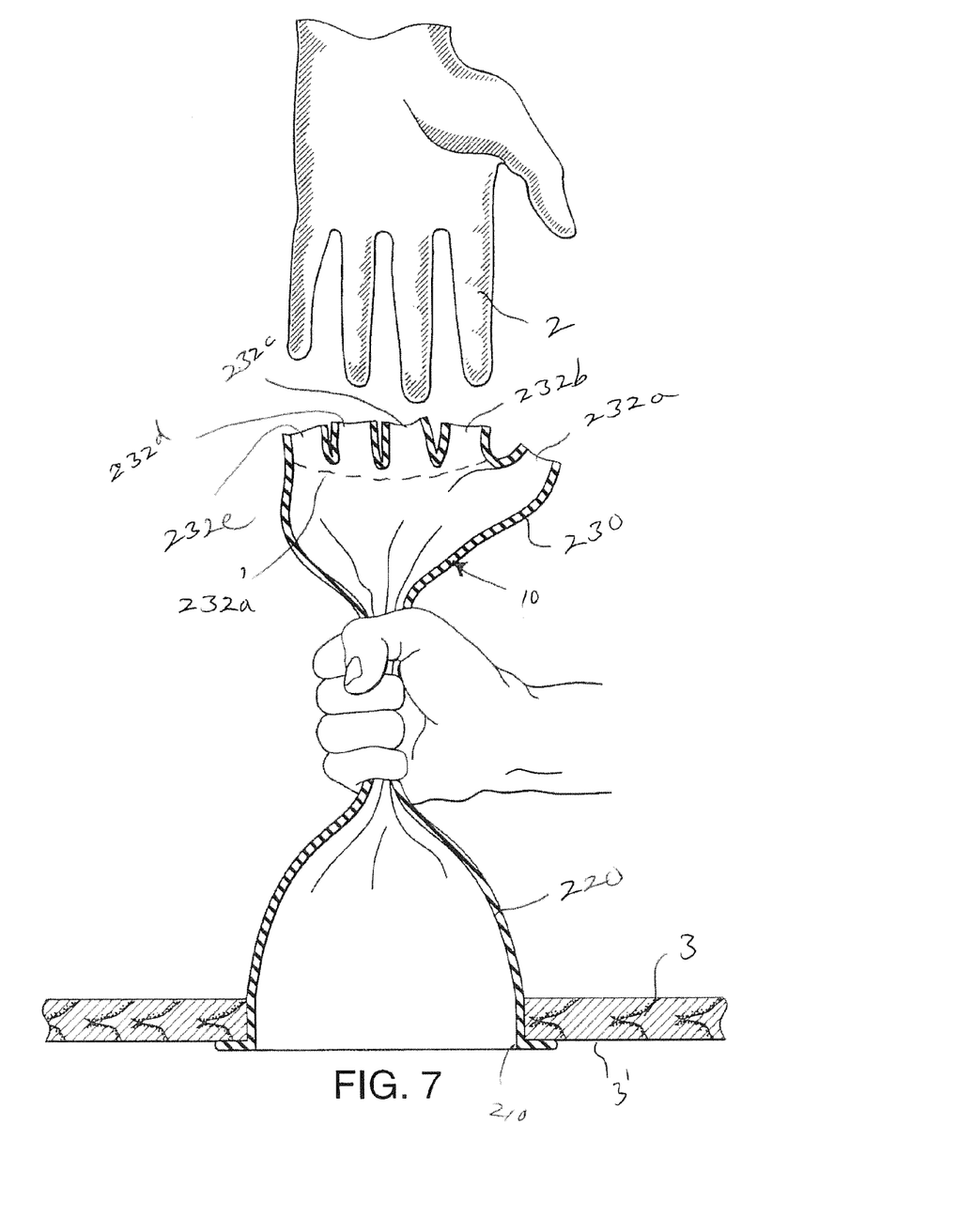

FIGS. 6-7 illustrate how one surgeon's gloved hand may be removed from the outer glove portion of the disclosed device, without removing the device from its installed position within the sufflated body cavity. The intermediate wall of the outer glove portion is drawn inside out with the surgeon's hand when the hand is withdrawn from the cavity. Another hand may be used to grip the intermediate wall as shown in FIG. 7 to pinch the wall there and retain the sufflated cavity's seal while the withdrawn hand is fully removed from the outer glove portion. Another surgeon may then insert their gloved hand into the outer glove portion by passing the thumb and fingers through respective openings. Once the outer glove portion is fully and snuggly worn up to the wrist like this, the pinched closure of the intermediate wall may be released and the gloved hand reinserted into the sufflated body cavity, as illustrated in FIGS. 2 and 2A to continue the surgical procedure.

Thus, in addition to preserving the sensitivity and dexterity of the fingers and thumb, use of the disclosed apparatus affords the surgeon and his/her surgical team great operational flexibility during a procedure requiring manuary access to a sufflated cavity. The means for gaining manuary access may be left in place and re-used for multiple access by the same surgeon or by different surgeons. Since each accessing surgeon's hand is already covered by a surgical glove, removal and insert of the gloved hand may occur without fear of compromising sterility as a result. Therefore, colleagues in the same operating room cooperatively participating in the surgical procedure on the same patient may share the outer glove apparatus. One surgeon can pull his/her gloved hand out and another surgeon can place his/her gloved hand inside and still retain the full benefits of the manuary access apparatus.

Another advantage is that since the outer glove portion of the apparatus is largely digitless, it presents a simpler device to manufacture. The manufacturing process to suitably form the precise and relatively complicated structure for accommodating the fingers and thumb tends to be proportionally more complicated. Hence, the manufacturing process required for the disclosed device will invariably be quite simpler, and therefore less costly, especially in such embodiments as shown in FIGS. 1A and 1B where the fingers share a large common opening while only the thumb occupies a smaller dedicated opening.

The simpler, digitless structure also removes a restriction in terms of size and fit. Since finger length and thickness are highly variable between individuals, the digitless outer glove portion (where at most the base and very trunk of the fingers are covered by the outer glove portion) makes the apparatus much more amenable to a one-size fits all construction/configuration. This is all the more so where the outer glove portion is formed with a truncated mitten type configuration with the fingers collectively passed through a large shared opening, such that the outer glove portion may approach universal fit given sufficiently resilient material compositions. Otherwise, wide ranges of different sized glove portions would be required to accommodate the different thumb and finger sizes. As variables like finger length and thickness or thumb length and thickness are obviated, the apparatus is normally rendered a much more universal in configuration and readily adaptable device for use by any individual, except those having excessively aberrant hand and finger sizes/configurations/attributes.

Referring again to FIG. 1, there is shown one embodiment of the subject manuary access apparatus 10. Manuary access apparatus 10 generally includes a seal section 100 coupled to a sheath section 200. Seal section 100 is preferably formed with an endless loop configuration realized with any suitable shape known to sufficiently effect sealed engagement with a soft bodily tissue surface. In the embodiment shown, seal section 100 is preferably formed with a ring-shaped contour which defines an annular engagement surface whose arcuate sectional contour may effectively maintain sealed engagement with the smooth, yet non-flat, tissue lining surfaces typically encountered within a human anatomy. Seal section 100 is preferably formed with a resilient bias towards an annular or other encircling configuration about an opening 120, such that it readily springs to its original configuration once it is fully introduced into a patient's internal body cavity after undergoing deflection and deformation during passage through an incision-formed fenestration.

Seal section 100 is fabricated by any suitable means known in the art of a resilient material that is substantially impermeable to both liquid and gas. It is preferably formed of a material containing rubber, plastic, or any other suitable composition which exhibits sufficient resilience and liquid/gas impermeability. The material is preferably one which is capable of withstanding continuous extended exposure to the biochemical environment that it would typically be subjected to during use in the intended application, and which tends not to cause irritation or other significant ill effects in the bodily portions it contacts during that use.

Seal section 100 is preferably fabricated separately and joined to sheath section 200 via a thermally welded joint or via any other suitable measures known in the art. Seal section 100 may, alternatively, be integrally formed with sheath section 200. It is important, in any event, that sufficient measures be taken to avert the compromise in either the strength or seal realized at the joint (or transition region) between the sections 100, 200.

Sheath section 200 is generally formed as a protective covering for the surgeon's hand and forearm to be introduced into the given body cavity. As such, it is formed generally of a flexible, pliable material substantially impermeable to liquid and gas which closely conforms to at least the hand inserted therein, but does not substantially constrict nor restrict the movements of either the hand or forearm.

Sheath section 200 includes a mouth portion 210 coupled to loop portion 110 of seal section 100; an outer glove portion 230; and, a pliable intermediate portion 220 collapsibly extending therebetween. Mouth portion 210 is preferably formed to follow the endlessly looped contour of loop portion 110, such that it defines an opening which coincides with opening 120. Mouth portion 210 is intimately coupled to loop portion 110 in sealed manner by either integral formation therewith or by any suitable adjoining measure. The coupling itself is of sufficient strength and durability to resist compromise when subjected to various stresses during use upon manipulations of the intermediate and glove portions 220, 230.

Extending from and preferably formed integrally with mouth portion 210 is a pliable intermediate section 220. As it serves in accordance with the present invention to reconfigurably maintain, during use, a barrier substantially impermeable to gas across the space immediately surrounding the surgeon's hand and forearm, it is important that intermediate section 220 be readily collapsible and extendable. Those properties enable intermediate section 220 to adaptively reconfigure responsive to hand and forearm movements while preserving the seal established across the hand-admitting fenestration.

Preferably, intermediate section 220 is formed of a thin material containing a plastic, rubber, or other liquid/gas impermeable material of suitable strength, durability, and pliability. It is preferably of sufficiently low material weight that it may be freely drawn partially inside out to accommodate the mouth portion's insert into the body cavity (with seal section 100) prior to the glove portion's insert. It is preferably of such sufficiently low material weight, also, to freely yet captively extend responsive to the pressure of the sufflation gas from the internal body cavity which would otherwise escape through the fenestration when the surgeon's hand is admitted therethrough. As the surgeon's hand and forearm are moved within the fenestration and body cavity during the course of surgery, then, intermediate section 220 reconfigurably captures a surrounding pocket of sufflation gas.

Preferably, though certainly not essentially, intermediate section 220 is formed of a translucent material. In addition to permitting the entry of illuminating light into the body cavity, this enhances the visibility into the cavity available to the surgeon.

The outer glove portion 230 is formed of a material having the liquid/gas impermeability, strength, and durability of the other portions 210, 220. It is preferably formed, however, of a sufficiently elastomeric material to snugly conform to the surgeon's pre-gloved hand 2 (wearing a surgical glove whose cuff 2' is indicated within the intermediate section 220). The sensitivity and mobility of the surgeon's gloved hand digits remain substantially unhindered because they pass in this embodiment through respective truncation openings 232a-232e which terminate the outer glove portion 230, as shown in FIG. 2.

Figure 1:
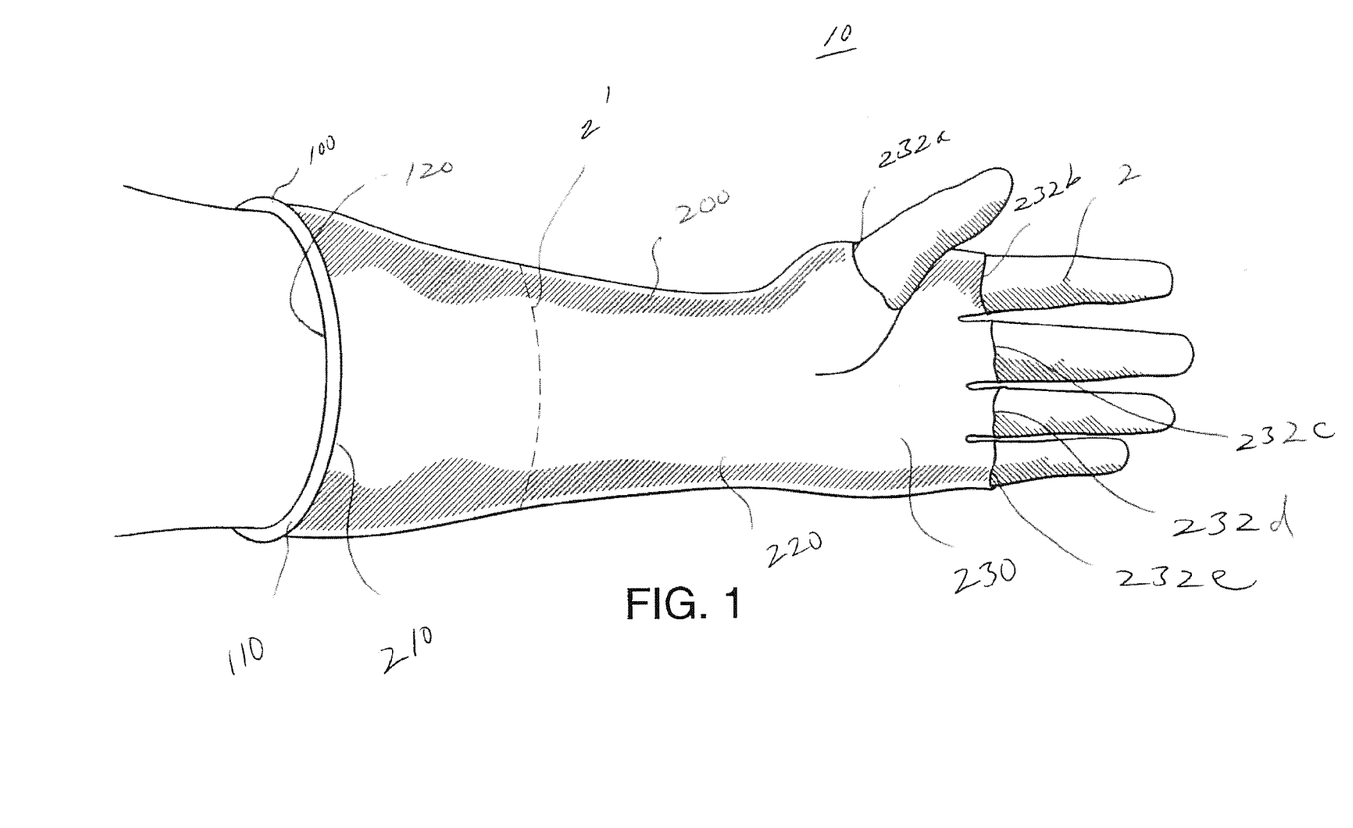
FIG. 1 is a perspective view of an apparatus formed in accordance with one exemplary embodiment of the present invention, with the apparatus fully stretched for illustrative purposes over a gloved hand of a user.
Figure 1A:
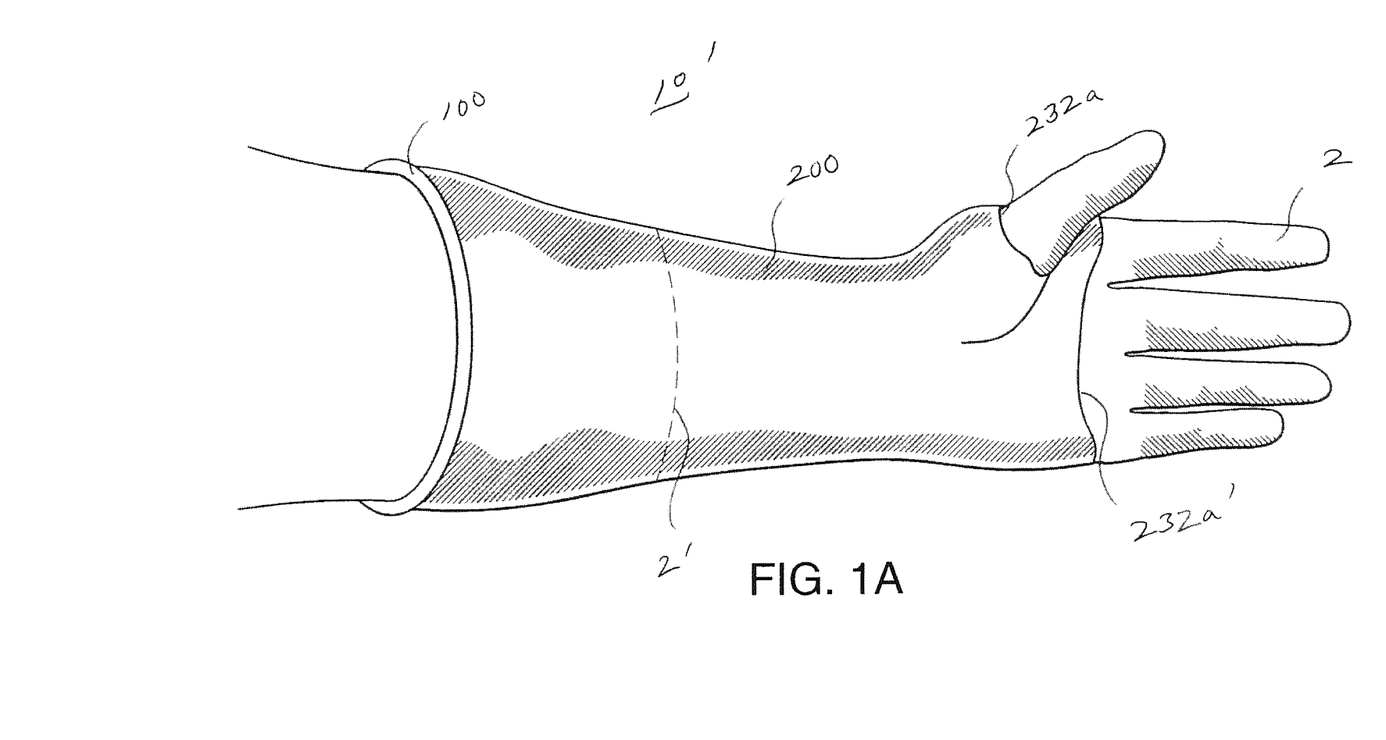
FIG. 1A is a perspective view of an apparatus formed in accordance with a another exemplary embodiment of the present invention, with the apparatus fully stretched for illustrative purposes over a gloved hand of a user.
Figure 1B:
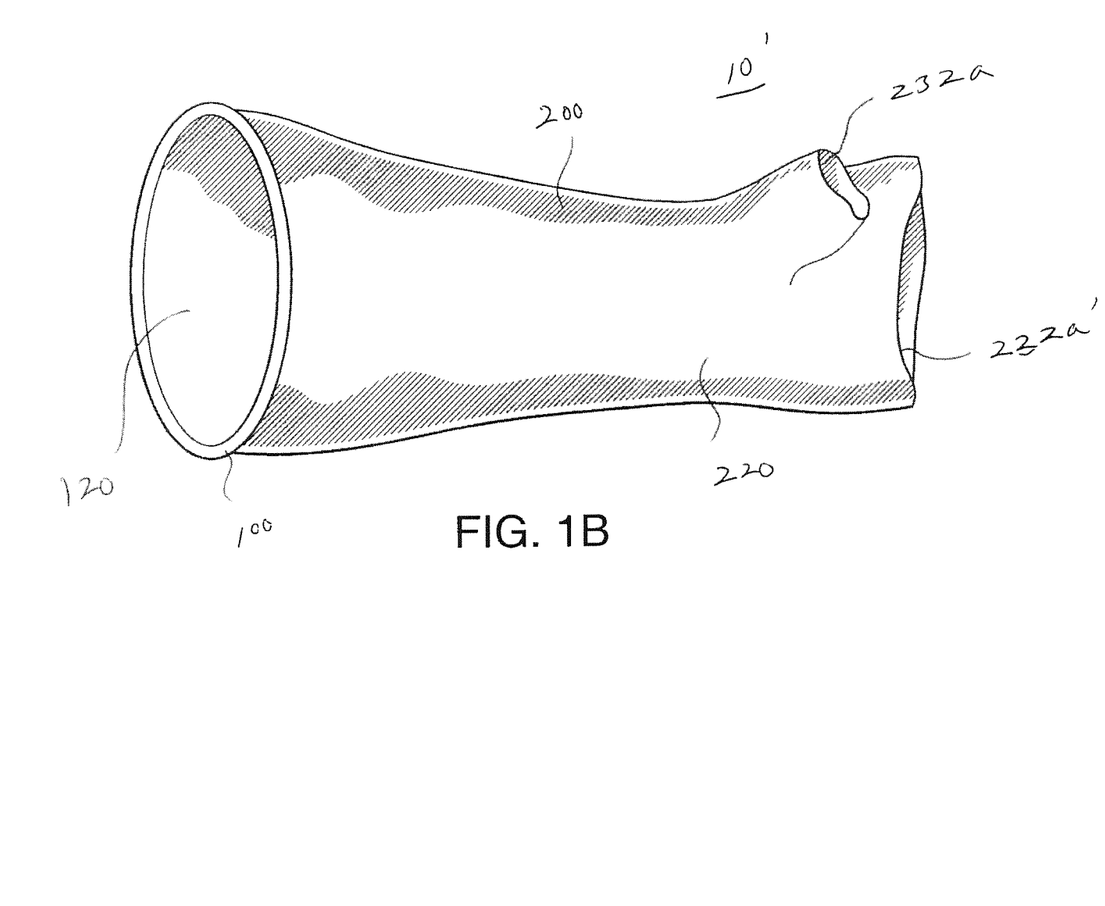
FIG. 1B is a perspective view of the embodiment of FIG. 1A, with the apparatus in isolation shown fully stretched for illustrative purposes.

The exemplary embodiment of apparatus 10' illustrated in FIGS. 1A-1B and 2A is similar in all respects to the embodiment of FIG. 1, and like elements are identified by like reference numbers and characters. The difference in this embodiment is that the glove portion 230 is configured with but two truncation openings, a first opening 232a to accommodate the thumb and a second opening 232a' to accommodate all of the fingers together. The open sheath, or truncated mitten, configuration which results maximizes the universality of fit, ease of use, freedom of dexterous movement, and ease of manufacture. In each of the FIGS. 2 and 6-7, both embodiments—with respective openings 232b-232e for the fingers individually, and with one shared opening 232a' for the fingers collectively—are shown and comparatively indicated for illustrative purposes.

In FIGS. 1-1A, the rear most parts of the intermediate portion leading to the loop portion 110 are shown to extend beyond the cuff 2' of the surgeon's gloved hand 2. But this merely shows for illustrative purposes the apparatus 10, 10' stretched out fully over the surgeon's arm. During use, the loop portion 110 remains inserted within the patient's internal body cavity, and the parts of the intermediate portion 220 proximate thereto will remain near the fenestration, below the surgeon's forearm. So contact between that intermediate portion 220 and a part of the forearm not covered by the surgical glove does not occur normally. Added measures be taken in this regard to guard against such occurrence. For example, the surgical glove worn by the surgeon may be configured so that its cuff 2' extends well up the forearm to preclude the unwanted contact.

The outer glove portion 230 may be formed in any suitable manner known in the art—in much the same manner, for instance, that typical latex surgical gloves are formed. In accordance with the present invention, however, it is important that glove portion 230 be coupled at its cuff region to intermediate portion 220. It may be integrally formed with intermediate portion 220, or else, intimately joined thereto at a sealed joint (not shown) by any suitable means known in the art, such as by thermal welding or other techniques.

In an exemplary abdominal cavity application of apparatus 10, 10' illustrated in FIGS. 2 and 2A, manuary access into a patient's abdominal cavity 1 is gained through a fenestration 2 formed by incision through the patient's skin and underlying layers of tissue—collectively referred to herein as the "abdominal wall" 3 in the application illustrated. Seal section 100 is passed through the fenestration 3" and positioned beneath the abdominal wall 3 to bear against, and form a substantially sealed engagement with, the abdominal wall's inner lining layer 3'—the peritoneum in the case of the abdominal cavity. To accommodate this, sheath section 200 is at least partially drawn to an inside-out configuration. Once the surgeon's gloved hand 2 is inserted into sheath section 200, fitted through the outer glove portion 230, and thereafter admitted into the abdominal cavity 1 through the opening 120 of seal section 100 as shown, intermediate portion 220 forms a gas-capturing pocket 225 about the surgeon's gloved hand 2. Sufflation gas (normally maintained at a regulated pressure within the abdominal cavity 1 during surgical procedures) that might otherwise escape through open portions of the fenestration about the surgeon's hand 2, is then retained by the pocket 225. Subsequent movements of the surgeon's hand 4 cause the redistribution of the sufflation gas trapped within the pocket 225, but do not cause its escape.

The retention of sufflation gas by intermediate portion 220 at the pocket 225 provides another advantage in accordance with the present invention. The upward force applied to seal section 100 by the sufflation gas pressure, or intra-abdominal pressure, maintained within the abdominal cavity 1 which urges it against the inner lining of the abdominal wall 3 is further augmented by the entrapment of sufflation gas at the pocket 225. The sufflation gas pressure at that pocket 225 causes intermediate portion 220 to draw seal section 100 upward, thereby reinforcing its sealed engagement of the abdominal wall 3 inner lining.

If left unchecked, however, the collective upward force upon apparatus 10 could very well lead to its expulsion from the fenestration altogether. Thus, in accordance with the present invention, the passage of sheath section 200 through the opening 120 of seal section 100 (into the abdominal cavity 1) forced by the surgeon's hand 4 and glove covered forearm deflects sufflation gas migrating between the abdominal cavity 1 and the pocket 225 against that part 220' of intermediate portion 220 lining the soft body tissue peripherally bounding the fenestration, as indicated by the directional arrows 7. This yields an outwardly directed pressure which biases the part 220' into substantially conforming engagement of the fenestration-bounding body tissue. Both the device's seal preserving capability and its retention within the fenestration are thereby augmented. Thus, apparatus 10, 10' serves to securely preserve an uninterrupted seal across the fenestration 3', while affording substantially free mobility to both the surgeon's gloved hand and forearm within the confines of the fenestration 3' and abdominal cavity 1.

The simplicity of apparatus 10, 10', both in structure and function, affords other significant advantages which may not be readily apparent. For instance, its spacial requirements during use do not extend significantly beyond a fenestration broad enough to admit the surgeon's hand and forearm. This yields as much surrounding area of the abdominal or other given surface on the patient's body to accommodate the separate fenestrations necessary for the passage of other instruments into the given internal body cavity. Hence, the 'overcrowding' of the surgery area typically encountered in hand-assisted minimally invasive procedures is considerably minimized—along with the attendant safety risks of inadvertent interference of neighboring instruments, restricted ranges of mobility, and the like.

Figure 3:
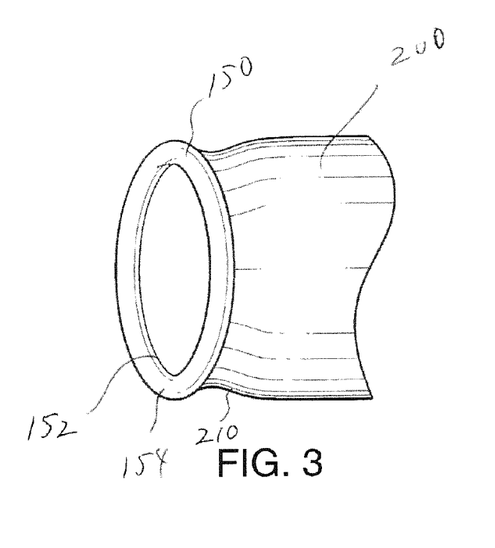
FIG. 3 is a perspective view, partially cut away, of a portion of an alternate exemplary embodiment of a portion incorporated in the apparatus as shown in FIGS. 1 and 1A.
Figure 4:
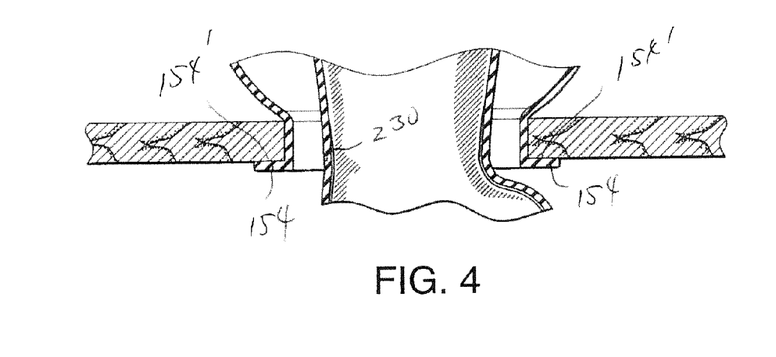
FIG. 4 is a sectional view of the embodiment shown in FIG. 3 illustrating an exemplary configuration during use.

Referring now to FIGS. 3-4, there is shown a seal section 150 formed in accordance with an alternate embodiment of the present invention. While preferably similar in material composition and properties as seal section 100 described with reference to the embodiments shown in FIGS. 1-2A, seal section 150 in this embodiment includes an annular collar portion 152 coupled as before to mouth portion 210 of sheath section 200. Seal section 150 further includes an outwardly flared flange portion 154 extending from collar portion 152, whose upper surface 154' engages the inner lining of the abdominal wall 3 in substantially flush manner.

Figure 5:
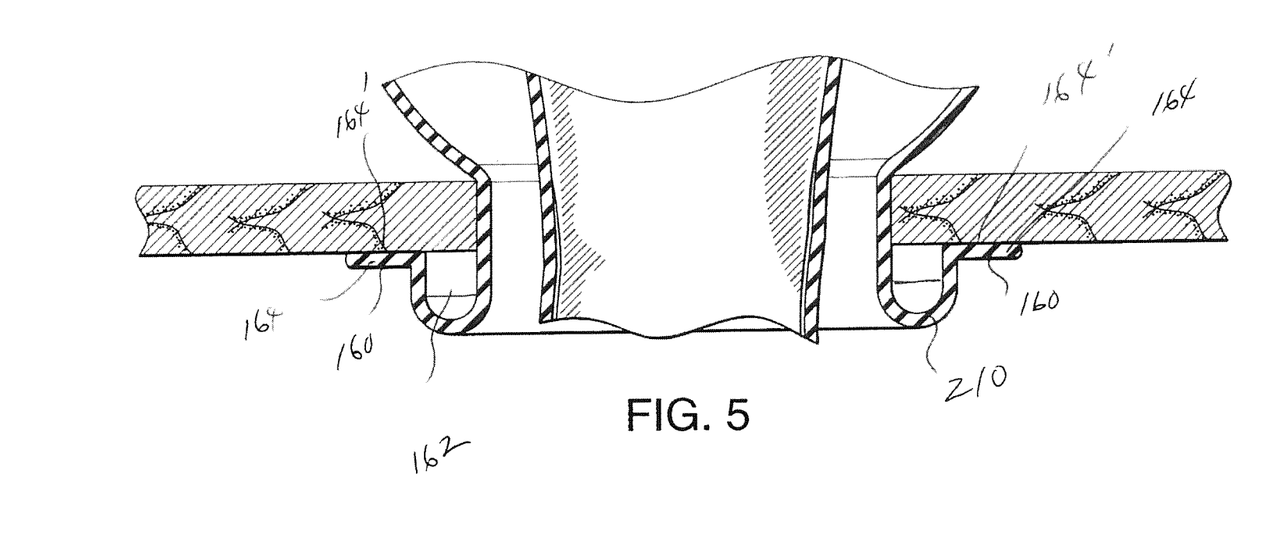
FIG. 5 is a sectional view of another alternate exemplary embodiment of a portion incorporated in the apparatus as shown in FIGS. 1 and 1A, illustrating an exemplary configuration during use.

Numerous other configurations may be employed for the seal section. In another alternate embodiment shown in FIG. 5, for example, seal section 160 is similar in configuration to seal section 150 shown in the embodiment of FIGS. 3-4, but orientated in inverted manner relative to intermediate section 200 and dimensioned accordingly. Seal section 160 includes an annular collar portion 162 coupled to mouth portion 210 of sheath section 200. Seal section 160 further includes an outwardly flared flange portion 164 extending from collar portion 162, whose upper surface 164' engages the inner lining of the abdominal wall 3 in substantially flush manner.

FIGS. 6-7, in conjunction with FIGS. 2 and 2A, illustrate use of the apparatus 10, 10' during a surgical procedure requiring manuary access as disclosed herein. In FIG. 1, a surgeon's gloved hand 2 has gained manuary access into the sufflated body cavity by passage through the outer glove portion 230. When the user wishes to temporarily interrupt the manuary access, he/she may withdraw the accessing hand 2 from the internal body cavity, as illustrated in FIG. 6. The outer glove portion 230 will then pull out with the hand 2 back through the mouth portion 210 which remains in place (since the seal section 100 remains in sealed engagement with the abdominal wall's inner lining layer 3'). Part of the intermediate portion 220 also pulls back out with the outer glove portion 230 yielding an inside out withdrawl through the mouth portion 210.

As illustrated in FIG. 7, the surgeon may then grasp the withdrawn part of the intermediate portion 220 to pinch and constrict the same there. The gas-capturing pocket 225 formed beneath the pinched part substantially holds the sufflation seal in tact and permits the surgeon to de-couple and fully remove the surgically gloved hand 2 (just withdrawn from manuary access) from the outer glove portion 230. The same surgeon or another individual may then replace their surgically gloved hand back into the outer glove portion 230, appropriately adjust the fit, then re-insert that portion and the trailing part of the intermediate portion 230 with the gloved hand 2 back in through the mouth portion 210 and into the internal body cavity to resume manuary access, as required for the given procedure.

Although this invention has been described in connection with specific forms and embodiments thereof, it will be appreciated that various modifications other than those discussed above may be resorted to without departing from the spirit or scope of the invention as defined in the appended claims. For example, functionally equivalent elements or processes may be substituted for those specifically shown and described, certain features may be used independently of other features, and in certain cases, particular locations of the elements or processes may be reversed or interposed, all without departing from the spirit or scope of the invention as defined in the appended claims.

What is claimed is:

1. An apparatus for maintaining manuary access to a sufflated body cavity through a fenestration in selectively arrestable manner during a minimally invasive surgical procedure, comprising:
   (a) a seal section including an endless loop portion defining a first opening, said loop portion having formed thereon an engagement surface for engaging in substantially flush manner an inner wall surface of the sufflated body cavity adjacent the fenestration; and
   (b) a sheath section formed of a substantially gas impermeable material, said sheath section including:
      (1) a mouth portion coupled to said loop portion of said seal section, said mouth portion defining a second opening aligned in open communication with said first opening;
      (2) inner and outer glove portions formed of an elastomeric material, said outer glove portion defining at least two digit receiving sections each terminated by a truncation opening for respectively passing a thumb and fingers of a user's hand covered by said inner glove portion and resiliently engaging base portions of the covered thumb and fingers in a sealed manner; and
      (3) a pliable intermediate portion extending between said mouth and outer glove portions to maintain therebetween a substantially gas impermeable barrier for defining a gas capturing pocket when said outer glove portion is passed through said first and second openings into the body cavity responsive to manuary actuation, said gas capturing pocket receiving sufflation gas migrating from the body cavity to distend adaptively about said outer glove portion, said intermediate portion configured to be withdrawn from the sufflated body cavity beyond said seal section and crimped without interrupting the substantially flush engagement of said seal section with the sufflated body cavity inner wall surface;
   wherein said inner glove portion is thereby removable from said outer glove portion without interrupting said substantially flush seal section engagement;
   whereby the sufflation of the body cavity is substantially preserved during the minimally invasive procedure.

2. The apparatus as recited in claim 1 wherein said outer glove and intermediate portions of said sheath section are integrally joined.

3. The apparatus as recited in claim 2 wherein said sheath section is formed of a composition including a plastic material.

4. The apparatus as recited in claim 3 wherein said sheath section is formed of a substantially translucent material.

5. The apparatus as recited in claim 2 wherein said sheath section is formed of a composition including a rubber material.

6. The apparatus as recited in claim 5 wherein said seal section is formed of a resilient material.

7. The apparatus as recited in claim 6 wherein said engagement surface of said seal section loop portion includes an outwardly extended flange.

8. The apparatus as recited in claim 7 wherein said loop portion of said seal section is substantially annular in contour.

9. The apparatus as recited in claim 6 wherein said loop portion of said seal section is contoured substantially as an annular ring.

10. The apparatus as recited in claim 1 wherein said outer glove portion is formed with a mitten type configuration defining a first digit receiving section terminated by a truncation opening for passing the thumb of the user's gloved hand and a second digit receiving section terminated by a second truncation opening configured to be shared by remaining fingers of the user's gloved hand for combined passage therethrough.

11. A hand covering apparatus for maintaining manuary access to a sufflated body cavity of a patient through a fenestration formed in the patient's body tissue in selectively arrestable manner during a minimally invasive surgical procedure comprising:
   (a) a resilient seal section including an endless loop portion, said loop portion defining a first opening and having formed thereon an engagement surface for engaging in substantially flush manner an inner wall surface of the sufflated body cavity about the fenestration; and
   (b) a sheath section formed of a substantially gas impermeable material, said sheath section including:
      (1) a mouth portion coupled to said loop portion of said seal section, said mouth portion defining a second opening aligned in open communication with said first opening;
      (2) inner and outer glove portions formed of an elastomeric material, said outer glove portion defining at least two digit receiving sections each terminated by a truncation opening for respectively passing a thumb and fingers of a user's hand covered by said inner glove portion and resiliently engaging base portions of the covered thumb and fingers in a sealed manner; and
      (3) a pliable intermediate portion integrally joined to said outer glove portion, said intermediate portion extending between said mouth and outer glove portions for defining a gas capturing pocket when said outer glove portion is passed through said first and second openings into the body cavity, said gas capturing pocket during the minimally invasive procedure receiving sufflation gas migrating from the body cavity to distend adaptively about said outer glove portion, said gas capturing pocket remaining at least partially withdrawn from the fenestration and engaging in substantially conforming manner the soft body tissue bounding the fenestration, said intermediate portion configured to be withdrawn from the sufflated body cavity beyond said seal section and crimped without interrupting the substantially flush engagement of said seal section with the sufflated body cavity inner wall surface;

wherein said inner glove portion is thereby removable from said outer glove portion without interrupting said substantially flush seal section engagement;

whereby said intermediate portion adaptively maintains a substantially gas impermeable barrier across portions of the fenestration about the user's gloved hand to substantially preserve the sufflation of the body cavity.

12. The apparatus as recited in claim 11 wherein said mouth and intermediate portions of said sheath section is integrally joined.

13. The apparatus as recited in claim 12 wherein said loop portion is configured substantially as an annular ring.

14. The apparatus as recited in claim 13 wherein said sheath section is formed of a composition including a plastic material.

15. The apparatus as recited in claim 13 wherein said sheath section is formed of a composition including a rubber material.

16. The apparatus as recited in claim 12 wherein said loop portion of said seal section includes an annular flange, said annular flange defining said engagement surface.

17. The apparatus as recited in claim 16 wherein said sheath section is formed of a composition including a plastic material.

18. The apparatus as recited in claim 16 wherein said sheath section is formed of a composition including a rubber material.

19. The apparatus as recited in claim 11 wherein said outer glove portion is formed with a mitten type configuration defining a first digit receiving section terminated by a truncation opening for passing the thumb of the user's gloved hand and a second digit receiving section terminated by a second truncation opening configured to be shared by remaining fingers of the user's gloved hand for combined passage therethrough.

\* \* \* \* \*